United States Patent [19]

Moore et al.

[11] 4,171,453

[45] Oct. 16, 1979

[54] CARBONATION OF ALKALI METAL PHENATES

[75] Inventors: Eugene R. Moore; David C. McDonald; Joseph Willner; Roger L. Briggs, all of Midland, Mich.

[73] Assignee: The Dow Chemical Company, Midland, Mich.

[21] Appl. No.: 879,935

[22] Filed: Feb. 22, 1978

[51] Int. Cl.$^2$ .............................................. C07C 65/10
[52] U.S. Cl. .................................... 562/406; 562/477
[58] Field of Search ................................ 562/406, 477

[56] References Cited

PUBLICATIONS

Encyclopedia of Chem. Technology, vol. 17, (1968).
Chem. Reviews, 57:583–620, 1957.
Chem. Abst. 70:37 482e (1969).
Chem. Abst. 123977y, Fr. 1,539,527.

*Primary Examiner*—Paul J. Killos
*Attorney, Agent, or Firm*—Michael L. Glenn

[57] ABSTRACT

A dry alkali metal phenate can be more efficiently carbonated with carbon dioxide under pressure to an alkali metal carboxylate of a phenol, if the phenate is finely divided and the temperature during carbonation is maintained below about 135° C. until at least about 25 mole percent of the carbon dioxide theoretically necessary to achieve complete carbonation is absorbed by the phenate. This method of carbonation is particularly useful to produce the sodium salt of salicylic acid.

7 Claims, No Drawings

CARBONATION OF ALKALI METAL PHENATES

BACKGROUND OF THE INVENTION

This invention relates generally to the carbonation of alkali metal phenates and relates more particularly to the carbonation of sodium phenate which produces the sodium salt of salicylic acid.

It is well-known that hydroxy aromatic carboxylic acids can be prepared by the reaction of alkali metal phenates with carbon dioxide in the absence of water. See Lindsey et al., *Chemical Reviews*, 57:583–620 (1957). In this reaction, dry finely divided alkali metal phenate is generally contacted with carbon dioxide at superatmospheric pressures at temperatures of from about 100° C. to about 300° C. over a period of hours to produce the corresponding carboxylic acid derivative. Under these conditions, however, the alkali metal phenate has a tendency to cake or agglomerate into larger particles resulting in inefficient mixing, lower yields of the acid salt product, and localized heating in excess of the desired temperature range leading to the formation of undesirable by-products. Various techniques are employed in the art to avoid this agglomeration, as is illustrated in British Pat. No. 1,205,447.

An inert solvent or suspension system can be employed to disperse the alkali metal phenate into smaller particles which are more efficiently carbonated, as illustrated in U.S. Pat. No. 2,824,892 and British Pat. Nos. 734,622 and 738,359. However, such techniques necessitate the difficult removal and recovery of solvents from the product. This solvent removal/recovery step is relatively expensive and limits the use of such solvents in industrial carbonation processes.

The more common practice in industry has been to employ rotary "ball mills" in the carbonation of sodium phenate to produce salicylic acid. In this method loose pieces of iron or stainless steel are employed inside the rotating mill to grind the aggregate particles into a smaller, more reactive particle size. These "ball mills", however, are difficult to maintain, can contaminate the product with metal fragments, require a large vessel to compensate for the volume occupied by the grinding medium, and are very noisy. Further, the removal of the carbonated product from the mill is difficult and time consuming because the product is not free-flowing. Therefore, it is necessary to rotate the mill during removal of the product.

The foregoing prior art methods for maintaining the relatively higher surface area and higher reactivity of the alkali metal phenate are relatively ineffective or uneconomical. It would be desirable, then, to provide an economical method of carbonation whereby the phenate could be predominantly maintained in a state conducive to carbonation, and whereby the carbonated product can be conveniently removed from the carbonation vessel.

The practice of this invention is useful to efficiently prepare hydroxy aromatic carboxylic acids from phenols. This carbonation process is particularly useful to prepare salicylic acid from phenol.

SUMMARY OF THE INVENTION

Carbonation of a dry, alkali metal phenate in the solid phase with carbon dioxide under pressure to an alkali metal carboxylate of the corresponding phenol is improved in a two-step carbonation process. In the first step, carbon dioxide contacts a finely divided solid alkali metal phenate at a temperature less than about 135° C. until at least about 25 percent of the stoichiometric amount of carbon dioxide is absorbed by the phenate. In the second step, the temperature is elevated above about 135° C. so as to effect further monocarbonation of the phenate.

Surprisingly, practice of the present invention can produce the alkali metal salt of the hydroxy aromatic carboxylic acid as a comparatively free flowing product in good yield using a high pressure reaction vessel equipped merely with a centrifugal agitation means for solids, such as a ribbon blender or other centrifugal mixer consisting of a rotor with a suitable mixing element. The practice of the present invention permits the use of mixing means for solids which are more efficient than the crude rotary ball mills employed by the prior art in dry carbonation processes. Heretofore, the use of these relatively more efficient mixing means was inhibited by the tendency of the alkali metal phenate to agglomerate during carbonation.

DETAILED DESCRIPTION OF THE INVENTION

The alkali metal phenates used as a starting material in the practice of this invention is an alkali metal salt of any phenolic compound (i.e., a mononuclear aromatic carbocyclic compound containing at least one nuclear hydroxyl substituent). The alkali metal phenates suitable for the practice of the method of this invention can bear other nuclear substituents so long as such substituents are inert in the process and so long as there is at least one reactive site for carbonation. Inert groups include, for example, alkyl groups, halogen groups, amino groups, hydroxyl groups or nitro groups, and the like. Phenates containing no more than one other substituent in addition to the hydroxyl group are preferred and unsubstituted phenates are most preferred. Suitable salts of phenolic compounds include, for example, the sodium and potassium salts of phenol, cresol or chlorophenol, and the like. The phenate reactant can be a single compound or mixture of compounds (e.g., position isomers), if desired. The novel process is most advantageously employed with sodium phenate to produce high purity sodium salicylate in good yield.

The alkali metal phenate carbonated by the method of this invention may be prepared by any of several known processes. Advantageously, all steps in which the phenate is present prior to carbonation are performed under an inert atmosphere, such as nitrogen, to prevent degradation of the oxygen-sensitive phenate. One method which can be used to produce said phenate comprises reacting an alkali metal hydroxide with a suitable phenolic compound in an aqueous solution or otherwise in a manner well-known in the art. Less desirably, a suitable phenolic compound can be reacted with the alkali metal directly. The alkali metal phenate can conveniently be extracted in a water phase and then dried.

The finely divided particles to be carbonated by the method of this invention advantageously should have a surface area of at least about 1 square meter per gram, move advantageously at least about 2 square meters per gram, as determined by nitrogen adsorption as taught in Johne et al., *Chem.-Ingr.-Techn.*, 37:57 (1965). The method of carbonation of this invention is not limited to the use of finely divided alkali metal phenate prepared by any particular method. One convenient method of obtaining finely divided particles with an exceptionally high surface area is to introduce an atomized spray of an aqueous solution of an alkali metal phenate into a stream of a hot inert gas, such as nitrogen gas, at a temperature of at least about 140° C. If the phenate reactant is prepared by a method which produces larger particles, it can be ground to a finely divided phenate prior to carbonation.

The dry finely divided alkali metal phenate can be carbonated in a continuous or batch process. The phenate reactant is normally carbonated in a high pressure reaction vessel equipped with a means for agitating solids and a means for heating and cooling the contents of the reaction vessel, such as a jacket containing a suitable heat transfer media. Thorough mixing and temperature control are facilitated by using loads of phenate in the range of from about 25 to about 50 volume percent of the reactor capacity. The agitating means is not necessarily critical, so long as the means provides sufficient mixing so as to effect during carbonation suitable heat transfer within the mass of alkali metal phenate. Suitable heat transfer is effected where substantially all of the phenate reactant is maintained at less than about 135° C. throughout the first step of the instant process. For example, in an operable, but less desirable embodiment, the phenate can be carbonated in a bed fluidized with carbon dioxide and optionally an inert gas such as nitrogen to promote heat transfer. Advantageously, a centrifugal agitating means can be employed to promote heat transfer. The mixing element of the centrifugal agitator can take any convenient shape such as a ribbon or plowshare. A rotary ball mill is a suitable, but not a desirable agitation means in the practice of this invention because of the relatively inefficient mixing effected thereby and the difficulty in removing the carbonated product.

Step 1

The first step of the carbonation reaction is carried out at a temperature less than about 135° C. However, because the carbonation reaction is exothermic, it is difficult to maintain the temperature of the contents of the reaction vessel below about 135° C. until the stipulated amount of carbon dioxide is absorbed by the phenate reactant, if carbonation is initiated at a temperature near this upper temperature limit. Carbonation is initiated, as the term is employed herein, when carbon dioxide is brought together with the alkali metal phenate.

Carbonation is preferably initiated in the first step at a temperature of from about 20° C. to about 110° C., more preferably about 30° C. to about 80° C. Initial temperatures lower than those in the aforementioned preferred ranges are operable, but undesirable because of the energy wasted in cooling the reactants. The contents of the reaction vessel, that is the alkali metal phenate and its carbonation products, are advantageously mixed during carbonation so as to maintain substantial thermal equilibrium and to substantially eliminate regions where the desired temperature range is exceeded.

After carbonation is initiated, the temperature of the contents of the reaction vessel are maintained at a temperature limit below about 135° C. until at least about 25 percent of the stoichiometric amount of carbon dioxide necessary to effect monocarbonation is absorbed by the phenate. The amount of carbon dioxide absorbed is conveniently approximated by subtracting the amount of carbon dioxide present at the measured temperature and pressure in the free volume in the reaction vessel from the amount of carbon dioxide charged therein. The free volume being the volume of the reaction vessel less the volume of the phenate present at its absolute density.

Advantageously, carbon dioxide is introduced into the reaction vessel at a substantially constant rate. The introduction of carbon dioxide is controlled so that the temperature is not raised too rapidly by the exothermic carbonation reaction. Generally, it is preferred that the temperature of the contents of the reaction vessel is limited in this first step to a temperature below about 120° C. until about 40 percent, more preferably below about 115° C. until about 50 percent of the theoretical amount of carbon dioxide necessary to achieve 100 percent conversion is absorbed by said phenate so as to prevent agglomeration of said phenate. In converting sodium phenate to sodium salicylate, absorption of more than about 75 percent of the theoretical amount of carbon dioxide at a temperature less than about 135° C. produces significantly higher amounts of the impurity sodium para-hydroxy benzoate. Hence, it is desirable in the carbonation of sodium phenate to produce sodium salicylate to absorb an amount of carbon dioxide in the range from about 40 to about 75 mole percent below a temperature of about 135° C., preferably below about 120° C.

Step 2

After the alkali metal phenate has absorbed the specified amount of carbon dioxide, the temperature of the contents of the reaction vessel is increased in the second step of the method of this invention to effect more rapid monocarbonation of the phenate. Carbonation temperatures of from about 150° C. to about 250° C. are generally suitable in this second step, with temperatures from about 180° C. to about 210° C. being preferred. In the carbonation of particular alkali metal phenates certain temperature ranges are preferred in the art and are generally advantageously employed to effect carbonation of specific phenates to the corresponding hydroxy aromatic carboxylate in the practice of the method of this invention. To illustrate, in the carbonation of sodium phenate it is preferable to maintain a temperature in the range from about 180° C. to about 210° C. in this second step of the carbonation to produce sodium salicylate in good yield; these higher temperatures reduce the weight percentage of an undesirable by-product, sodium p-hydroxybenzoate.

The carbon dioxide pressures in Steps 1 and 2 above are not critical to the practice of the method of this invention. Generally, superatmospheric pressures are employed during the carbonation, but any carbon dioxide pressure can be employed which effects carbonation of the alkali metal phenate at an acceptable rate and which produces the hydroxy aromatic carboxylic acid in good yield. In the first step of this method pressures of from about 0.1 to about 100 pounds per square inch absolute (psia) are preferred, but these pressures need not be effected immediately upon the initiation of carbonation due to the absorption of a substantial amount of carbon dioxide. Also during this first step, the carbon dioxide pressure can (and generally will) fluctuate due to the interruption of the carbon dioxide flow into the reaction vessel to prevent the temperature from exceeding about 135° C. In the second step of this carbonation higher carbon dioxide pressures in some cases increase the reaction rate with a consequent improvement in yield for a given reaction time. In the carbonation of specific alkali metal phenates certain ranges of carbon dioxide pressure may be preferred in the art and can advantageously be employed in the second step of the method of this invention to carbonate said phenate. To illustrate in the carbonation of sodium phenate the rate of carbonation suddenly increases at a temperature in the range of 135° C. to about 150° C. as can be observed as a sudden drop in the carbon dioxide pressure. Advantageously, less than a minute after the drop in pressure is observed the flow of carbon dioxide into the reaction vessel can be increased so as to effect a higher pressure and more rapid carbonation of the phenate. Preferably, the ultimate pressure in the sodium phenate carbonation is in the range from about 40 to about 500 pounds psia and is effected slowly over a period of at least about 20 minutes or more to avoid the agglomeration of the product.

The duration of carbonation required to effect substantial conversion of the alkali metal phenate is dependent on such parameters as the carbonation temperature, the pressure of carbon dioxide, the specific alkali metal phenate being carbonated, and the desired yield of the salt of the hydroxy aromatic carboxylic acid. In general, the yield of the hydroxy aromatic carboxylate will increase with increasing carbonation times up to the point at which equilibrium is reached between the phenate and carbonated species. If all other parameters remain constant, incremental units of time have a decreasing impact on yield as this equilibrium point is approached. The duration of carbonation is not critical, so long as a suitable yield of the carbonated product is produced. Typically a carbonation time of about 2 hours to about 10 hours is suitable.

After carbonation has proceeded to the desired extent, the pressurized carbon dioxide is conveniently vented and the reaction vessel purged with an inert gas, e.g., nitrogen. The instant two-step process is now complete. The alkali metal carboxylate of a phenolic compound produced in this process can now be purified by conventional methods known to the art.

It is generally desirable to effect substantially complete monocarbonation in a single two-step carbonation to promote efficiency of operation. However, in an operable, but less desirable embodiment of the instant two-step process a lower degree of carbonation can be effected. The unreacted phenate can be separated and cycled back into the carbonation process to increase the overall yield of the carbonated product.

In contrast to the carbonated product of prior art techniques, the hydroxy aromatic carboxylate produced by the instant two-step process is predominantly a free-flowing powder, i.e., a free-flowing particulate mass that moves readily with a continual change of place among the constituent particles in falling toward a lower center of gravity for the mass. Comparatively little agitation of the free-flowing product is required to destroy the static state of the particles and set them in motion. Consequently, the free-flowing product can be readily removed from the reaction vessel.

The product of the instant two-step process, which is an alkali metal salt of a hydroxy carboxylic acid, can be readily acidified in a manner known to the art. Conveniently, said salt can be acidified by bringing it together with a strong mineral acid, such as sulfuric acid or hydrochloric acid, in an aqueous solution. While the foregoing methods of acidification of the alkali metal salt are convenient, the instant carbonation process does not extend to and therefore is not limited by any particular method of acidification following carbonation.

The hydroxy aromatic carboxylic acid can be recovered after acidification and purified by methods well-known in the art. Generally, the acids are precipitated from a cold aqueous solution, collected and dried. Salicylic acid can be readily purified by sublimation as is illustrated in U.S. Pat. Nos. 1,987,301 and 1,987,382.

The following examples re presented to illustrate, but not in any manner limit the invention.

Procedure in Examples

Sodium phenate is carbonated with carbon dioxide under pressure in a ten cubic foot reaction vessel equipped with a stainless steel ribbon blender driven by a motor and a heating jacket. The reaction vessel is heated by means of steam introduced into the reaction vessel jacket from a source pressurized at 165 psia. Cooling of the reaction vessel is effected by introducing water into the jacket. The reaction vessel is also connected to vacuum and carbon dioxide lines as well as 5 internal temperature sensing devices positioned just above the phenate prior to agitation as well as in the phenate. The solids temperature reported in the experiments is taken from a thermocouple kept free of any insulating phenate by the mixing element. Care must be observed in the placement of a thermocouple in the reaction vessel to avoid false readings of the temperature of the phenate due to poor mixing and poor heat transfer of the phenate in contact with the thermocouple.

The sodium phenate carbonated in these experiments is prepared by bringing together equimolar amounts of sodium hydroxide and phenol in an aqueous solution at reactive conditions. The solution of sodium phenate is then spray dried in a stream of nitrogen at about 200° C. and the finely divided sodium phenate collected. Analysis of the phenate disclosed a surface area of from 2.5 to 3.5 square meters per gram, whereas phenate dried in a rotary ball mill typically has a surface area one-fifth as great. The phenate is loaded into the reaction vessel under vacuum and the vessel equilibrated at 100° C. for one hour and then is equilibrated at the initial carbonation temperature. The ribbon blender is rotated at about 60 revolutions per minute in the experiments to sweep out 20 reactor volumes per minute. The carbon dioxide line is then opened and the gas introduced slowly to prevent the exothermic reaction from proceeding too rapidly. After about five minutes the flow of carbon dioxide is increased to about 1.5 percent of the theoretical amount introduced per minute. The reaction vessel is eventually pressurized to 100 psig with the addition of carbon dioxide occurring over a period of about five hours. The experiments indicate the heating or cooling cycle employed in the individual carbonation runs.

The carbonation product is recovered after the reactor is vented, purged with nitrogen, and cooled to less than 90° C. unless otherwise indicated. The product is then analyzed by liquid chromatography of the acidified product for organic compounds and analyzed by neutron activation for sodium. The percentage yield in moles of sodium salicylate based on sodium phenate is then calculated from the foregoing analyses on the basis of the ratio of sodium salicylate to sodium in the product. The yield of a hard-to-remove impurity, sodium para-hydroxybenzoate, is calculated in an analogous manner.

EXAMPLE 1

Sodium phenate is carbonated in a manner consistent with the Experimental Procedure section. The reactor is loaded with a sodium phenate charge of about 70 pounds in a first run and about 100 pounds in a second and a third run.

In the first run, which is not an embodiment of the method of this invention, the carbonation is initiated at about 80° C. In this first run the contents of the reaction vessel are permitted to freely exotherm effecting a maximum temperature of about 161° C. at which time about 25 percent of the moles of carbon dioxide required for complete carbonation of the phenate is absorbed. Over the carbonation period of 5 hours, 31 pounds of carbon dioxide is absorbed and a maximum pressure of about 73 psia is effected. The product of this carbonation is visibly coarse in texture and contains large lumps.

In the second run, which is an embodiment of the method of this invention, the carbonation is also initiated at 80° C. In this second run cooling water at a temperature of about 30° C. is circulated in the jacket of the reactor and the flow of carbon dioxide is controlled to maintain a maximum temperature of about 130° C. until about one-half of the theoretical amount of carbon dioxide is absorbed. The temperature of the contents of the reaction vessel is increased gradually above 130° C. with the carbon dioxide flow turned off until a sudden pressure drop is registered. The carbon dioxide flow is turned on and gradually increased so as to reach a pressure of about 80 psia in five minutes and a constant value of about 115 psia shortly thereafter. The temperature of the contents of the reaction vessel increases as the exothermic carbonation continues to a maximum temperature of about 205° C. The product is a finely divided powder visibly indistinguishable from the starting material.

In the third run the carbonation is once more initiated at about 80° C. in an embodiment of this invention. The temperature of the contents of the reactor are cooled with 30° C. water in the jacket to maintain a temperature of about 80° C. as the sodium phenate slowly absorbs about one-half of the carbon dioxide necessary to effect theoretically complete conversion. The contents of the reaction vessel are then reacted with carbon dioxide at higher temperatures effected by the exothermic reaction and steam heating to a maximum of about 165° C. The product is a finely divided powder visibly indistinguishable from the starting material.

The sodium salicylate and sodium para-hydroxybenzoate yields as a mole percentage of the sodium phenate are tabulated in Table I.

TABLE I

| Run Number | Na Salicylate (%) | Na p-Hydroxybenzoate (%) |
|---|---|---|
| 1* | 32.0 | 6.1 |
| 2 | 82.5 | 0.2 |
| 3 | 81.0 | 5.1 |

*Not an embodiment of this invention.

It is apparent from the data in Table I and visual examination of the carbonation product in the three runs, that the sodium phenate aggregates into large lumps when the temperature is not carefully regulated during carbonation resulting in a poor yield of carbonated product. On the other hand, carbonation of sodium phenate with centrifugal agitation in the practice of the method of this invention produces finely divided sodium salicylate in excellent yield. Higher maximum temperatures in the second carbonation step reduce the contamination of the product with sodium para-hydroxybenzoate.

EXAMPLE 2

Sodium phenate is carbonated in a first run in accordance with the method set out in the second run of Example 1 immediately above. In a second carbonation in accordance with the practice of the method of this invention, the sodium phenate is carbonated as in the first run except that the carbon dioxide pressure is increased to about 165 psia in the second step of the carbonation and the maximum temperature consequently increases to 215° C.

A sample of the product in both of the runs is removed for analysis at the end of five hours of carbonation in the first run and after 4 hours of carbonation in the second run. The molar percentages of sodium salicylate, of sodium para-hydroxybenzoate are tabulated in Table II.

TABLE II

| Run Number | Na Salicylate (%) | Na p-Hydroxybenzoate (%) |
|---|---|---|
| 1 | 82.5 | 0.20 |
| 2 | 76.0 | 0.18 |

What is claimed is:

1. In the carbonation of a dry, alkali metal phenate in the solid phase with carbon dioxide under pressure to the alkali metal carboxylate of the corresponding phenol, the improvement wherein the carbonation is a two-step process which comprises:
    (a) in the first step, carbon dioxide contacts a finely divided solid alkali metal phenate at a temperature less than about 135° C. until at least about 25 percent of the stoichiometric amount of carbon dioxide is absorbed by the phenate; and
    (b) in the second step, the temperature is elevated above about 135° C. so as to effect further monocarbonation of the phenate.

2. The improvement of claim 1 wherein the alkali metal phenate during carbonation is agitated by a centrifugal agitation means for solids.

3. The improvement of claim 1 wherein the alkali metal phenate is sodium phenate and the alkali metal carboxylate of the corresponding phenol is sodium salicylate.

4. The improvement of claim 3 wherein the sodium phenate during carbonation is agitated by a centrifugal agitation means for solids.

5. The improvement of claim 4 wherein the finely divided sodium phenate carbonated is prepared by spray drying a solution of sodium phenate in a hot nitrogen stream to effect a surface area of at least about 2 square meters per gram of phenate.

6. The improvement of claim 5 wherein in the first step a molar amount of carbon dioxide equivalent to from about 40 to about 75 percent of the moles of said phenate present prior to carbonation is absorbed by said phenate before elevating the temperature above 120° C.

7. A process for preparing sodium salicylate comprising:
    (a) in a first step, contacting with carbon dioxide and agitating with a centrifugal solids agitation means for finely-divided sodium phenate having a surface area of at least about 2 square meters per gram, said sodium phenate being maintained at a temperature less than about 135° C. until a molar quantity of carbon dioxide equivalent to about 40 to about 75 percent of the moles of said phenate present prior to carbonation is absorbed by the sodium phenate; and (b) in a second step, elevating the temperature of the sodium phenate above about 135° C. and introducing carbon dioxide as necessary to effect a pressure of about 40 to about 500 psia.

* * * * *